United States Patent [19]
Fuisz

[11] Patent Number: 5,370,881
[45] Date of Patent: Dec. 6, 1994

[54] WATER-SOLUBLE DELIVERY SYSTEMS FOR HYDROPHOBIC LIQUIDS

[75] Inventor: Richard C. Fuisz, Great Falls, Va.

[73] Assignee: Fuisz Technologies Ltd., Chantilly, Va.

[21] Appl. No.: 81,338

[22] PCT Filed: Oct. 30, 1992

[86] PCT No.: PCT/US92/09447
§ 371 Date: Jun. 29, 1993
§ 102(e) Date: Jun. 29, 1993

[87] PCT Pub. No.: WO93/08699
PCT Pub. Date: May 13, 1993

Related U.S. Application Data

[60] Continuation-in-part of Ser. No. 787,245, Nov. 4, 1991, abandoned, which is a continuation-in-part of Ser. No. 602,485, Oct. 24, 1990, Pat. No. 5,096,492, which is a division of Ser. No. 283,742, Dec. 13, 1988, Pat. No. 5,011,532, which is a continuation-in-part of Ser. No. 169,838, Mar. 18, 1988, Pat. No. 4,855,326, which is a continuation-in-part of Ser. No. 40,371, Apr. 20, 1987, abandoned.

[51] Int. Cl.$^5$ .......................... A23L 3/30; A23L 1/09; A23L 1/22
[52] U.S. Cl. .................................. 426/5; 426/658; 426/549; 426/650; 426/651; 424/48; 424/49; 424/401; 424/484
[58] Field of Search ........................ 426/3-6, 426/658, 96, 549, 650, 651; 424/48, 49, 401, 484

[56] References Cited

U.S. PATENT DOCUMENTS

| | | | |
|---|---|---|---|
| 3,595,675 | 7/1971 | Ash et al. | 426/576 |
| 3,615,671 | 10/1971 | Shoaf et al. | 426/590 |
| 3,723,134 | 3/1973 | Chivers | 426/660 |
| 3,930,043 | 12/1975 | Warning et al. | 426/515 |
| 4,496,592 | 1/1985 | Kuwahara et al. | 426/5 |
| 4,855,326 | 8/1989 | Fuisz | 426/658 |
| 4,873,085 | 10/1989 | Fuisz | 426/658 |
| 4,978,537 | 12/1990 | Song | 426/5 |
| 5,004,595 | 4/1991 | Cherukuri et al. | 426/5 X |
| 5,011,532 | 4/1991 | Fuisz | 426/660 |
| 5,096,492 | 3/1992 | Fuisz | 426/658 |
| 5,108,762 | 4/1992 | Broderick et al. | 426/5 |
| 5,116,627 | 5/1992 | Rutherford et al. | 426/5 |
| 5,165,944 | 11/1992 | Song et al. | 426/5 |
| 5,198,251 | 3/1993 | Song et al. | 426/5 |

*Primary Examiner*—Jeanette Hunter
*Attorney, Agent, or Firm*—Hoffmann & Baron

[57] ABSTRACT

A solid delivery system for rapid release of hydrophobic liquids such as oleaginous materials, flavor oils, mineral oil and the like comprising a water-soluble flash-flow-formed matrix containing a micronized dispersion of a substantially hydrophobic liquid.

41 Claims, 5 Drawing Sheets

3% PEPPERMINT OIL IN
97% MALTRIN-365
500 X

FIG. I

3% PEPPERMINT OIL IN
97% MALTRIN-365 (CRYOGROUND)
1250 X

3% PEPPERMINT OIL IN
97% PALATINIT PF
500 X

3% PEPPERMINT OIL IN
97% PALATINIT (CRYOGROUND)
1250 X

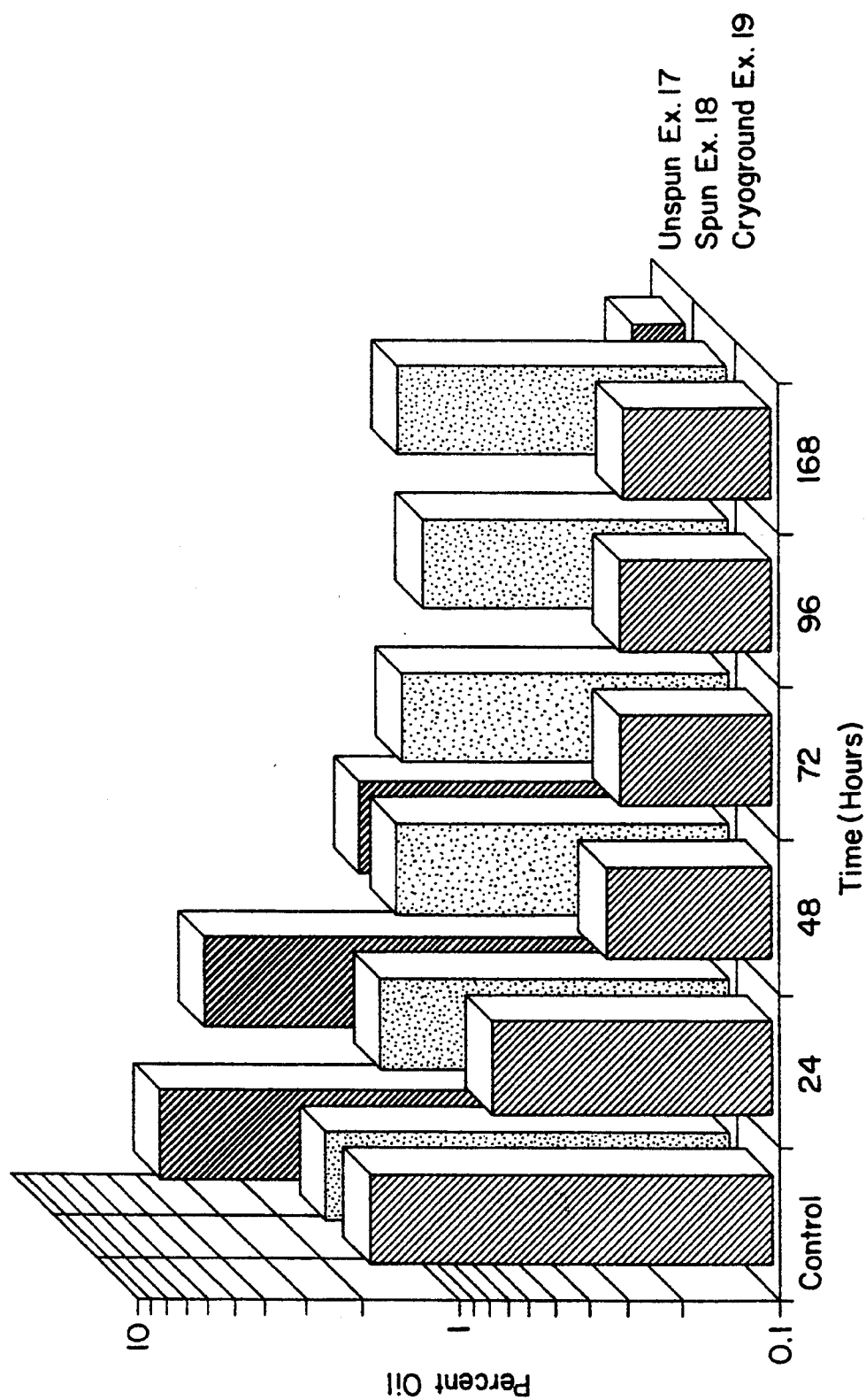

WATER-SOLUBLE DELIVERY SYSTEMS FOR HYDROPHOBIC LIQUIDS

CROSS-REFERENCED TO RELATED APPLICATIONS

The present invention is a continuation-in-part of Ser. No. 787,245 filed Nov. 4, 1991, now abandoned, which in turn is a continuation-in-part of Ser. No. 602,485 filed Oct. 24, 1990, now U.S. Pat. No. 5,096,492, which in turn is a division of Ser. No. 283,742 filed Dec. 13, 1988 now U.S. Pat. No. 5,011,532, which is a continuation-in-part of Ser. No. 169,838 filed Mar. 18, 1988 now U.S. Pat. No. 4,855,326, which is a continuation-in-part of Ser. No. 040,371, filed Apr. 20, 1987 now abandoned.

BACKGROUND OF THE INVENTION

The present invention is directed to a novel method of encapsulating finely divided or micronized, substantially hydrophobic fluids using flash-flow, e.g. melt-spun techniques, to produce delivery systems for use in food products and other comestibles, pharmaceuticals, gum and confectionery products, cosmetics and personal hygiene products. More particularly, the present invention relates to a delivery system having a solid, hydrophilic encapsulating material capable of undergoing those changes associated with the flash-flow phenomena occurring during, for example, melt spinning and having a multitude of finely divided or micronized hydrophobic oil dispersed therein.

The use of hydrophobic oils of flavorants or fragrances in comestibles, pharmaceuticals, cosmetics and the like has focused on ways to control the organoleptic impact either by delaying or accelerating the intensity of perception. In conventional comestible products such as foods, pharmaceuticals, gum and confectioneries, flavor oils have been added in the free state, as well as in the encapsulated form for the combined effects of immediate and delayed flavor perception. For example, U.S. Pat. No. 4,485,118 to Carrol, et al. discloses a chewing gum composition which contains sequentially released plural flavor system. One of the flavors is encapsulated with a water-insoluble coating for delayed release and a separate flavor is introduced in free, un-coated form for immediate release. U.S. Pat. No. 3,962,463 to Witzel discloses a chewing gum having a reduced content of flavor ingredients, obtained by impregnating or depositing solid flavor particles, such as microencapsulated flavor particles sorbed on an edible substrate, and placing them on the surface of the gum.

In the comestible art, encapsulation and coating techniques have also focused on protecting the flavor oils from reacting with other co-mixed chemicals, or from oxidation, evaporation or volatilization through direct exposure to the environment. Flavor oils have been combined with a variety of sweeteners, particularly, for example, in gum and confectionery products. Flavor oils are often aldehyde, ketone and ester compounds which are highly reactive with a host of other common materials found in comestible products, as well as being sensitive to heat. For example, one such material commonly added to comestibles which reacts quickly to lose its sweetness in the presence of flavor oils is aspartame. The result is a comestible product which lacks both flavor and sweetness and therefore suffers from lack of overall organoleptic quality and shelf-life instability.

Methods of encapsulating or coating oils have conventionally involved using matrices of other hydrophobic materials, such as melted and solidified fats and waxes, polymers such as polyvinyl acetate and solvents, and/or elastomeric materials. Simple mixtures of these hydrophobic matrices and flavor and/or sweetener materials were prepared using solvents and/or heat to form a melt in order to incorporate the flavor oil into the matrix. Incorporation in the melted stage was required to obtain as much homogeneity and encapsulation as possible. The molten mass was then cooled to solidification and ground into particles.

U.S. Pat. No. 4,740,376 to Yang discloses use of a melted high molecular weight polyvinylacetate blended with a hydrophobic plasticizer and a flavoring ingredient. The melt blend is cooled, ground into a particulate and incorporated into an edible product. The hydrophobic plasticizers employed are mono-, di- and triglycerides having a fatty acid chain length of 16 to 22 carbons.

U.S. Pat. No. 4,722,845 to Cherukuri, et al. discloses stable cinnamon flavored chewing gum compositions comprising gum base, sweetener and a sweetener delivery system comprising a dipeptide or amino acid sweetener in a mixture of fat and high melting point (106° C.) polyethylene wax. U.S. Pat. No. 4,803,022 also to Cherukuri, et al. discloses a powdered flavor composition encapsulated in a hydrophobic matrix of fat or wax and containing thaumatin, monellin or dihydrochalcones as the sweetener.

U.S. Pat. No. 4,824,681 to Schobel, et al. discloses an encapsulated sweetening agent which is protected from moisture and provides controlled release wherein the sweetening agent is encapsulated with a hydrophobic polymer and a hydrophobic plasticizer. Hydrophobic coating is also described in detail in U.S. Pat. No. 4,828,857 to Sharma, et al. wherein a delivery system is disclosed having as a core material a sweetener or flavoring ingredient and a protective matrix formed by a fluidized bed spray coating.

These processes involving the formation of molten hydrophobic mixtures having inherent disadvantages which include loss of volatile flavor components during the heating process and significant mixing requirements to ensure homogeneity. Separate grinding steps followed, which also generated vaporization of flavor components and, in the case of certain sensitive sweeteners, degradation and loss of sweetness. Additionally, simple mixtures have failed to provide adequate uniform coating protection to keep the core flavors and sweeteners in a sustained stabilized state. Other processes, in an attempt to improve over simple mixing techniques, have included spray congealing and fluidized bed spray coating. While these methods may overcome certain of the above-mentioned disadvantages, they still employ significant amounts of heat and/or solvents and plasticizers and do not result in micronized discrete flavor droplets within a matrix, but rather a non-uniform agglomeration of the flavor and/or sweetener with a hydrophobic carrier. See, for example, U.S. Pat. No. 4,722,845 to Cherukuri, et al. Coating of sweeteners and oils with hydrophobic materials also interferes with the immediate release properties and up-front, instantaneous flavor and/or sweetness impact.

The delivery systems of the present invention represents a departure from conventional methods and their resultant products in a number of important ways. To begin with, instead of using hydrophobic encapsulating matrix materials, flash-flowable hydrophilic materials are employed. These materials must be capable of undergoing flash-flow processes such as melt-spinning without significant degradation or burning. Therefore, instead of simple mixing and grinding, spray congealing and spray coating techniques, flash-flow processing as later defined herein, is employed. The result is a solid particulate which constitutes a highly water-soluble, flash-flowable matrix or encapsulant in which there is dispersed throughout fine, micronized liquid droplets. During the flash-flow process, the encapsulant is exposed to extremely limited conditions of heat and then usually only for a fraction of a second. This substantially lessens the potential for volatilization of certain hydrophobic liquid components. In the case of flavor oils, analytical testing has demonstrated that the intensive delivery systems retain more flavor components than those processes of the prior art.

SUMMARY OF THE INVENTION

The present invention concerns a method of producing encapsulated hydrophobic fluids, and the resultant delivery systems made therefrom. The oils are contained in and protected by encapsulation in a water-soluble, solid matrix made from flash-flowable materials such as sweetening agents and the like. The oil is present in the matrix in finely divided micronized droplets which are dispersed in and entrapped by the surrounding matrix. The encapsulated liquid particles result from the flash-flow process, e.g., by melt-spinning a mixture of a water-soluble matrix with the oil to produce flakes or floss particles which can be used "as is" or subsequently further divided into a fine powder. The powder is formed of particles which in turn constitutes a matrix of the water-soluble protective coating and a micronized oil dispersion contained therein.

The preferred matrix materials are sweetening agents which are readily processed through flash-flow processing techniques. In one preferred embodiment the delivery system employs flavor oils which are intended to be used in comestible products. The combination of a sweet tasting water-soluble matrix and flavor or aromatic oil dispersed throughout provides a synergistic effect due to the concurrent release of both constituents. It is believed that the immediate delivery of the oil in the mouth provides a flavor/sweetener impact which is not only more intense but more true to the original flavor oil taste. This effect is due to the fact that more flavor components have been retained during processing and give a higher perception of intensity due to their intimate contact with the flash-flowable sweetener.

The flavor oils may be chosen from a host of materials which are suitable for the chosen application. Peppermint oil, for example, is one such oil which is commonly used in chewing gum and confectionery products and which when incorporated into the present delivery system provides a means of protecting the oil from loss of volatiles and degradation, yet produces immediate, up-front flavor release when placed in the mouth or other aqueous medium.

In one aspect of the invention, a particulate delivery system having a hydrophilic liquid dispersion or core and a solid water-soluble matrix is produced by means of flash-flow processing. The delivery system can be used in a variety of products for delivering hydrophobic oils, and in particular, flavor, fragrance and other aromatic oils. The delivery system is especially useful for instant and immediate delivery of the core material upon contact with moisture, e.g., when placed in the mouth. One particular application involves the use of the delivery system as dusting powders for chewing gum, confectionery products and baked goods.

The delivery system of the present invention provides uniform distribution of the hydrophobic liquid composition and retains the volatile and unstable components of the liquids which contribute to the overall character of the liquid. In the case of flavor oils and various aromatic oils, essential volatile components such as flavor notes and aromas are retained during processing and captured in the final product, which results in a more flavorful or fragrant product with high authenticity and trueness to its intended taste and/or smell.

The flash-flow process is essentially instantaneous and vaporization and/or degradation of the hydrophobic liquid composition, including other components such as sweeteners or fibers carried therewith, is substantially, if not completely reduced when compared to conventional spray-drying processing and simple mixing.

The delivery system can be used in applications such as flavor and sweetener dusting powders without the use of anti-caking materials such as corn starch. The delivery system emerges from the flash-flow process in a number of different forms, such as floss or flakes, but can be ground, pulverized or sieved into a fine particulate or powder without substantial loss of hydrophobic liquid or other components contained in the matrix. Cryogrinding using nitrogen is the preferred method of comminution. The retention of oil components in the invention process is largely due to the fact that the liquid is in micronized form within the matrix rather than being simply adsorbed onto a carrier or enrobed within a coating.

The delivery systems also have a more uniform distribution of the hydrophobic liquid composition than can be achieved by simple mixing or spray drying techniques. One particular advantage is that a variety of flash-flowable materials can be used in conjunction with the hydrophobic oil to satisfy a host of applications. For example, spray-dried mixture of cyclodextrins and flavors can be combined with the flash-flowable matrix materials to provide enhanced flavor-delivery systems. The flash-flow-formed delivery system retains substantially all of its flavor components and can be cryoground to a uniform particle size distribution. Cryogrinding has the unique advantage over conventional grinding of reducing heat build-up and subsequent loss of volatiles. This allows for a greater uniformity in particle size and shape then ordinary grinding, where frictional heat build-up can be problematic. Very fine powders can be produced using flash-flow processing followed by cryogrinding. These powders can be directly applied to comestibles and have particular application as flavor/sweetener delivery systems useful in chewing gum compositions or dusting powders on gum and confectionery surfaces. These powders readily adhere to chewing gum surfaces during rolling and scoring of the gum due to the uniform particle size and shape.

For a better understanding of the present invention, references made to the following description and its scope will be pointed out in the appended claims.

BRIEF DESCRIPTION OF THE DRAWINGS

FIG. 5 is a graph showing a comparison of volatilization retention of the flash-flow formed delivery system, with and without cryogrinding, as compared to simple mixture encapsulation under controlled temperature conditions.

DETAILED DESCRIPTION OF THE INVENTION

Figure 1:
FIG. 1 is a photomicrograph (500×) showing micronized peppermint oil in a flash-flow-formed matrix of Maltrin-365.

The present invention concerns the formation of a new solid delivery system for rapid release of hydrophobic liquids. The delivery system includes a matrix of water-soluble flash-flowable material having a micronized dispersion of hydrophobic liquid contained therein. The matrix is designed to be protective of the oil during processing, with little or no substantial loss of oil components during the delivery system formation, yet be readily releasable of the oil components in conditions of moisture. In particular, the oils are immediately released in aqueous medium and especially when placed in contact with the oral cavity or other moist conditions in or on the body where rapid release of oil is desirable.

The hydrophobic liquid can be chosen from a variety of materials such as oleaginous liquids, flavor or aromatic oils as well as mineral oil, glycerin, polyethylene glycol, and the like. Examples of oleaginous liquids include, without limitation, vegetable oils, fish oils, lard, lanolin, cocoa butter and mixtures thereof. It will be appreciated that those hydrophobic materials which are solid at room temperature can be used provided they are rendered sufficiently liquid to be dispersed within the matrix during processing. Alternatively, in cases where the oleaginous material can be rendered to a dispersible state with pre-heating without destroying or losing desired volatile components, such limited pre-heating may be employed. For example, animal fats such as tallow, lard or hydrogenated animal and/or vegetable oils can be employed in the present invention.

Hydrogenation or partially hydrogenated vegetable oils useful in the present delivery systems include such materials as corn oil, canola oil, cottonseed oil, sesame oil, soybean oil, grape-seed oil, sunflower oil, safflower oil, rapeseed oil, olive oil, peanut oil and the like. These oils, as well as the animal fat oils are ingestible and are therefore most commonly used in comestibles.

Other hydrophobic oils include those referred to as flavor oils or essences. These oils are generally derived from plant extracts, although may alternatively be synthetically derived. Peppermint oil, spearmint oil, cinnamon oil, oil of wintergreen, citrus oils, and other fruit essences are the most commonly used flavor oils which are employed in the present invention. Flavor oils such as peppermint oil, spearmint oil and cinnamon oil are particularly harsh and crate a burning sensation in the mouth if ingested in too high a quantity. The present invention allows for the use of smaller quantities than in typically comestible applications if desired due to the synergy which is achieved with the sweetener matrix. The micronized dispersion gives the perception that a greater quantity of flavor is present than the actual amount, thereby enhancing both the organoleptic impact with less flavor oil and eliminating the need for higher amounts. This is particularly useful in applications such as chewing gum compositions, where the addition of flavor oil at high concentrations to achieve a more intense flavor impact results in plasticization of the gum base components and sloppy chew characteristics.

Examples of citrus or first oils and/or essences which are useful include a host of materials such as apple, apricot, banana, blueberry, cherry, grape, grapefruit, lemon, lime, orange, pear, peaches, pineapple, plum, raspberry, strawberry and the like. Mixtures and derivatives of these oils are contemplated.

Additional flavoring agents may be chosen from synthetic flavor oils and flavoring aromatics, and/or oils, oleo resins and extracts derived from plants, leaves, flowers, fruits and so forth, and combination thereof. For example, clove oil, bay oil, anise oil, eucalyptus oil, thyme oil, cedar leaf oil, oil of nutmeg, oil of sage, oil of bitter almonds and cassia oil may be used. Commonly used flavors include menthol, artificial vanilla, cinnamon derivatives, and various fruit flavors, whether employed individually or in admixture.

Flavorings such as aldehydes and esters including cinnamyl acetate, cinnamaldehyde, citral diethylacetal, dihydrocarvyl acetate, eugenyl formate, p-methylamisol, and so forth may also be used. Generally any flavoring or food additive such as those described in "Chemicals Used in Food Processing," pub 1274 by the National Academy of Sciences, pages 63–258 may be used.

Further examples of aldehyde flavorings include, but are not limited to acetaldehyde (apple); benzaldehyde (cherry, almond), anisic aldehyde (licorice, anise); cinnamic aldehyde (cinnamon); citral, i.e., alpha citral (lemon, lime); neral, i.e. beta citral (lemon, lime); decanal (orange, lemon); ethyl vanillin (vanilla, cream); hellotropine, i.e., piperonal (vanilla, cream); vanillin (vanilla, cream); alpha-amyl cinnamaldehyde (spicy fruity flavors); butyraldehyde (butter, cheese); valcraldehyde (butter, cheese); citronellal; decanal (citrus fruits); aldehyde C-8 (citrus fruits); aldehyde C-9 (citrus fruits); aldehyde C-12 (citrus fruits); 2-ethylbutyraldehyde (berry fruits); hexenal, i.e., trans-2 (berry fruits); tolyl aldehyde (cherry, almond), veratraldehyde (vanilla); 2,6-dimethyl-5-heptenal, i.e. Melonal (melon); 2,6-dimethyl-5-heptenal, i.e., Melanal (melon); 2,6-dimethyloctanal (green fruit); and 2-dodecenal (citrus, mandarin); cherry; grape, strawberry shortcake; mixtures thereof; and the like.

Other specific flavor compounds such as ethylacetate, thiophene, ethylpropionate, ehtyl butyrate, 2-hexanoate, 2-methylpyazine, heptaldehyde, 2-octanone, limonene, and eugenol are also useful.

The hydrophobic oil content of the present delivery systems is generally in the range of about 0.02% to about 40% by weight of the delivery system. However, deviations from this range are certainly possible provided that the micronized dispersion of the oil in the matrix results as a result of the flash-flow process. Preferably, the oils are present in amounts of about 0.05% to about 20% by weight of the delivery system and most preferably about 2% to about 12%.

The matrix materials can be selected from any material which is capable of undergoing those physical and/or chemical changes associated with flash-flow processing. Flash-flow processing has been described in a number of commonly owned patents such as U.S. Pat. Nos. 4,855,326, 5,001,532 and 5,096,492 from which the present application relates back, as well as 5,011,522 and 4,873,085, all of which are incorporated by reference herein.

Those materials useful as matrices may be chosen from such classes as sugars or sugar derivatives. These types of materials are preferred because of their flash-flow capabilities and their wide variety of applications. The term sugar is meant to include those carbohydrates having a high glucose profile. A high glucose profile means that the carbohydrate has a large number of six-carbon mono and disaccharides as well as other glucose-based oligomers. Mono-, di-, tri- and polysaccharides and their derivatives may be employed. Examples include glucose, sucrose, maltose, lactose, arabinose, xylose, ribose, fructose, mannose, pentose, galactose, sorbose, dextrose, sorbitol, xylitol, mannitol, pentatol, maltitol, isomalt, sucralose, maltodextrin, polydextrose and mixtures thereof.

Other matrix materials include cellulosics and starches and their chemical and biological derivatives. Cellulosics, however, are generally added in combination with mono- and disaccharide-based materials because the cellulosics are not as easily processed alone using flash-flow techniques.

The delivery systems of the present invention have a substantially amorphous flash-flow-formed matrix. The terms "flash-flow" refers to a process of subjecting the feedstock, e.g. matrix material and hydrophobic oil, simultaneously to flash heating and applied physical force such that the solid matrix material experiences sufficient internal flow to transform it to a physically and/or chemically altered structure from that of the feedstock.

Flash-flow processing can be accomplished several ways. Flash heat and flash shear are two such processes which can be used. In the flash heat process, the feedstock material is heated sufficiently to create an internal flow condition which permits part of the feedstock to move at a subparticle level with respect to the rest of the mass and exit openings provided in the perimeter of the spinning head. The centrifugal force created in the spinning head flings the flowing feedstock material outwardly from the head so that it reforms with a changed structure. The force required to separate and discharge flowable feedstock is only centrifugal force which results from the spinning head. The flash heat process is one process for producing an amorphous matrix such as the sugar floss used in this invention.

In the flash shear process, a shearform matrix is formed by raising the temperature of the feedstock material which includes a non-solubilized carrier to a point where the carrier such as a saccharide-based material undergoes internal flow upon application of a fluid shear force. The feedstock is advanced and ejected while in internal flow condition, and subjected to disruptive fluid shear forces to form multiple parts or masses which have morphology different from that of the original feedstock.

The multiple masses are cooled substantially immediately after contact with the fluid shear force and are permitted to continue in a free-flow condition until solidified.

The feedstock material which can be used in a flash shear process includes but is not limited to a carrier such as a saccharide-based material. Other materials such as oleaginous materials can also be included in the feedstock.

It is important that the feedstock selected for a flash shear process have the ability to be processed without reliance upon dissolution. In the case of a saccharide based material, the feedstock is primarily a solid material which is subjected to the flash shear process.

The flash shear process can be carried out in an apparatus which has means for increasing the temperature of a non-solubilized feedstock and means for simultaneously advancing it for ejection. A multiple heating zone twin screw extruder can be used for increasing the temperature and advancing feedstock. The second element of the apparatus is a means for ejecting the feedstock in a condition for shearing it to provide the shearform matrix. The means for ejecting is in fluid communication with the means for increasing the temperature and is arranged at the point to receive the feedstock while it is in the internal flow conditions. The means for ejecting the feedstock is preferably a nozzle which provides high pressure ejection of the feedstock material. For a description of various apparati which can be used to produce the inventive delivery systems, see copending U.S. Ser. No. 07/965,804, filed Oct. 23, 1992 entitled "Process for Making Shearform Matrix", which is herein incorporated by reference.

A preferred flash-flow process used to form the inventive delivery systems involves spinning a feedstock in a "cotton candy" fabricating type machine. The spinning machine used to achieve a flash heat process can be a cotton candy type machine, such as the Econo-Floss Model 3017 manufactured by Gold Metal Products Company of Cincinnati, Ohio. It will be appreciated by those skilled in the art that any apparatus or physical process which provides similar forces and temperature gradient conditions can also be used. For simplicity in disclosing and describing this invention, the terms "flash-heat" will be understood to mean a process which includes subjecting a feedstock to the combination of temperature, thermal gradients, flow, flow rates, and mechanical forces of the type produced in a cotton candy machine. The apparatus is operated at the temperature and speed which permit flash-flow of the feedstock without significant deterioration of ingredients including, for example, a crystallization control agent.

The matrix obtained in a melt-spinning process is in the form of a floss, fiber, particle, flake, spicule or any other generally non-descript amorphous aggregate. Disclosures which relate to spinning substances with one or more sugars are found in commonly-assigned U.S. Pat. Nos. 4,855,326, 4,873,085, 5,034,421, 4,997,856, 5,028,632, 5,034,421 and 5,096,492. These disclosures describe processing feedstock material by subjecting it to high speed spinning on a spinning head in which the substance is also subjected to heating against a heating element.

Additional additives can be added to the matrix/oil feedstock to achieve a variety of desired characteristics. These include, without limitation, fillers, humectants, emulsifiers, surfactants, coloring agents, flavors, fragrances, sweetening agents, flash-flowable polymers, plasticizers and the like.

As previously mentioned, the inventive delivery system can be used to provide enhanced flavor and/or sweetness delivery due to the flavor oil being finely dispersed in the sweetener matrix. The quality of the flavor as well as the intensity is more predictably released into the oral cavity due to the unique physical characteristics which are created during the flash-flow process.

By spinning the above-mentioned flavorant materials with the soluble melt spinnable carriers, even normally non-water soluble ingredients can be uniformly dispersed when contacted with water. The formation of the matrix is such that when added to a comestible such as chewing gum, for example, the flavor materials carried in the matrix rapidly dissolve when in contact with moisture. This unique property results in a dramatic flavor impact in the oral cavity.

In the case where two solid materials are to be used as the matrix, they may be combined prior to melt-spinning. For example, the matrix and the organoleptically perceivable material(s) may be combined by co-crystallization. Co-crystallization involves combining the ingredients in a heated state and thereafter allowing them to cool in a unified, crystallized manner. The unified structures are then reduced in size such as by being ground before being spun.

Other means of combining organoleptic perceivable materials with the matrix are also contemplated. For example, the matrix and flavorant may be combined in the spinning machine. In some cases, an oleaginous substance such as corn oil or polyvinylpyrrolidone (PVP), can be added to ensure uniform distribution of the flavor dispersion throughout the matrix of the spun product. For example, 2 parts oleaginous oil or a 2–3% solution of PVP may be added to the ingredients during the melt spinning.

The delivery system can also be compacted to less than 50% of the as-spun volume. Preferably, however, the delivery system is compacted to less than 30% and most preferably to less than 15% of the as-spun volume. As previously mentioned, the delivery system may also be reduced in particle size by milling before being added to comestibles.

The delivery system of the present invention has been found to be especially effective as a dusting powder or confectionery coating for chewing gum, confectioneries tablets, nougats, dragies and the like.

In the particular application with respect to chewing gum compositions, the delivery system can be used as a dusting powder on the surface of the gum product. The inventive powders have distinct advantages over dusting powders conventionally used for a number of reasons. The physical form of the inventive delivery systems allows for immediate release of the flavor oil components when placed in contact with the mouth. This has particular significance in that up-front impact is achieved. Additionally, due to the unique formulation of the oil dispersion within the matrix, the intensity and quality of the flavor can be more easily controlled. Furthermore, the micronized flavor oil droplets within a sweetener matrix gives the perception a fuller flavor with less actual flavor being present. Since the delivery system was formed using flash-flow processing, more flavor oil components remain than with conventional simple mixing or other encapsulation techniques. The sweetening agents used as the matrix serve as anti-sticking or anti-blocking agents during the gum making process, i.e., particularly in the rolling and scoring process.

The delivery system can be incorporated in conventional chewing gum compositions. These compositions typically contain a sweetener, a gum base and a flavor. The sweetener generally also serves as a bulking agent in sugared chewing gum compositions. One advantage of employing the inventive delivery system in chewing gum compositions is that the flavor can be directly incorporated with the bulking agent rather than in a separate step. Additional sources of flavor and/or sweetener can of course be combined with the delivery system and incorporated in the chewing gum composition.

With regard to the chewing gum compositions, the amount of gum base employed will vary greatly depending on various factors such as the type of base, consistency desired and other components used to make the final product. In general, amounts of about 5% to about 85% by weight of the final chewing gum composition are acceptable, with amounts of about 15% to about 30% by weight being preferred. The gum base may be any water-insoluble gum base well known in the art. Illustrative examples of suitable polymers in gum bases include both natural and synthetic elastomers and rubbers. For example, those polymers which are suitable in gum bases include, without limitation, substances of vegetable origin such as chicle, jelutong, gutta percha and crown gum. Synthetic elastomers such as butadiene-styrene copolymers, isobutylene-isoprene copolymers, polyethylene, polyisobutylene, polyvinylacetate and mixtures thereof are particularly useful.

The gum base composition may contain elastomer solvents to aid in softening the rubber component. Such elastomer solvents may comprise methyl, glycerol or pentaerythritol esters of rosins or modified rosins, such as hydrogenated, dimerized or polymerized rosins or mixtures thereof. Examples of elastomer solvents suitable for use herein include the pentaerythritol ester of partially hydrogenated wood rosin, pentaerythritol ester of wood rosin, glycerol ester of wood rosin, glycerol ester of partially dimerized rosin, glycerol ester of polymerized rosin, glycerol ester of tall oil rosin, glycerol ester of wood rosin and partially hydrogenated wood rosin and partially hydrogenated methyl ester of rosin, such as polymers of alpha-pinene or beta-pinene; terpene resins including polyterpene and mixtures thereof. The solvent may be employed in an amount ranging from about 10% to about 75% and preferably about 45% to about 70% by weight of the gum base.

A variety of traditional ingredients such as plasticizers or softeners such as lanolin, stearic acid, sodium stearate, potassium stearate, glycerol triacetate, glycerin and the like, including, natural waxes, such as paraffin waxes and microcrystalline waxes may also be incorporated into the gum base to obtain a variety of desirable textures and consistency properties. In accordance with the invention, however, these ingredients may be reduced in amount or in some cases, may be eliminated entirely. When present, these individual additional materials are generally employed in amounts of up to about 15% by weight and preferably in amounts of from about 3% to about 10% by weight of the final gum base composition.

The chewing gum may additionally include the conventional additives of coloring agents such as titanium dioxide; emulsifiers such as lecithin and glycerol mono-stearate; additional fillers such as aluminum hydroxide, alumina, aluminum silicates; calcium carbonate, and talc and combinations thereof; and additional flavoring agents. These fillers may also be used in the gum base in various amounts. Preferably, the amount of fillers when used will vary from about 4% to about 35% by weight of the final chewing gum.

The amount of delivery system used in the chewing gum composition will largely be a matter of preference. It is contemplated that the delivery system will be included in amounts of from about 0.25% to about 40% by weight of the final gum composition, with amounts of from about 1% to about 30% being preferred, and amounts of from about 1% to about 20% being most preferred.

In addition to the inventive delivery system, the chewing gum composition may also optionally include one or more additional ingredients such as conventional polysaccharide-based bulking agents including sugars or sugar alcohols, flavor delivery systems, spray-dried flavors, liquid flavors, natural and/or artificial sweeteners and the like.

An important feature of the chewing gum compositions prepared in accordance with the present invention is the ability of the delivery system to rapidly dissolve when in contact with the moisture present in the oral cavity. This feature significantly decreases the propensity of the flavor oil to become entrapped and solubilized within the insoluble chewing gum cud during mastication.

The chewing gum compositions of the present invention may be prepared by combining the water-insoluble gum base portion and the water-soluble flavor portion including the novel flavor/sweetener delivery system matrix according to conventional chewing gum processing techniques.

For illustrative purposes, a method of preparing the novel chewing gum compositions is as follows:

A suitable chewing gum base is first melted. Softeners and bulking agents such as sugar alcohols if desired may be added slowly with stirring thereafter. The inventive delivery system is then added and mixing is continued until a homogeneous mass is achieved. Optionally, additional flavor oils or spray dried flavors may be added as well. The mass may then be rolled, scored, dusted and wrapped in any manner known in the art.

With regard to the preparation of other types of comestibles, the spun matrix may also be added in a conventional manner. For example, in the case of pressed tablets, the flavor/sweetener delivery system may be dry blended with the remaining tablet ingredients and the mixture thereafter compressed into final tablet form. In the case of dentifrices, denture creams and cleansers, the products also benefit from incorporation of the delivery system in their formulations. In short, the matrix may be added to various comestibles in a manner similar to that which the skilled artisan currently uses to add conventional water-soluble comestible ingredients.

The present invention also provides for enhanced delivery of hydrophobic materials and allows these materials which are normally difficult to disperse in water, readily dispersible when placed in aqueous solution.

The delivery systems of the present invention can include a number of additional components which can be dispersed along with the hydrophobic liquid. These components can be pre-mixed with the liquid and added to the feedstock mixture of matrix and oil, or added concurrently with the matrix material and oil. For example, various sweeteners, such as natural or synthetic sweeteners can be combined with flavor oils by direct addition or in spray-dried form. Additionally, the flavor oil may be adsorbed on or incorporated in a carrier material prior to admixture with the matrix materials. Such carrier materials may include other flash-flowable materials or may be materials which are not easily flash-flow processed alone but can be added in amounts up to 50% of the total composition and combined with other more flash-flowable materials.

In one particular embodiment, micron-sized synthetic, amorphous silica has been used as a carrier for the hydrophobic liquids. These silicas have a unique combination of uniformity, chemical inertness, large surface area and porosity which make them highly adsorptive. These silicas can be manufactured with precisely controlled surface area, porosity and particle size distribution, which make them extremely useful in the inventive compositions. Commercially available silicas of this kind are sold under the trademarks SYLOID and SYLOX by W.R. Grace & Co., Baltimore, Md. These materials are specifically intended for use in dispersions and suspensions. Using these materials, flavor oils can be adsorbed onto their surfaces and into their pores and then added to the feedstock of matrix material to form the inventive delivery systems. In this manner, additional controlled release characteristics can be imparted to the delivery systems, as well as adding further stabilization and protective features to the oils against volatilization and oxidation. These silica compounds also have ionic and hydrogen bond affinity for certain flavor component chemical groups, which affinity serves to strengthen flavor retention and consequently allows for increased delayed release capabilities and stabilization characteristics.

Additional materials which can be as carriers for the flavor oils prior to incorporation with the inventive delivery system include maltodextrins, such as spray-dried maltodextrin marketed under the tradename M100 (10 DE) by Grain Processing Corporation, Muscatine, Iowa, as well as agglomerated maltodextrin (10 DE) sold under the tradename Micropor Buds 1015A, by E. Staley Manufacturing Co., Decatur, Ill. These materials are also porous and allow for flavor retention. Polydextrose and microcrystalline cellulose are also useful in this regard, as are a number of other adsorbent materials.

In one embodiment, the sweetener matrix or other matrix material can be combined with a cellulosic material such a microcrystalline cellulose and flash-flow processed. The resultant solid can then be further processed in accordance with present invention by adding artificial sweeteners and/or flavors and the like to it and again flash-flow processed.

Microcrystalline cellulose can also be used as the primary matrix material and combined with natural or artificial sweeteners, such as those enumerated herein, to form a delivery system which can be used "as is" or further combined with flavor oil and either flash-flow processed further or added directly to a comestible or other useful product, such as a pharmaceutical, cosmetic, dry food or drink mix, cereal, personal hygiene product or the like.

The present delivery systems are also useful in antacid compositions and especially those compositions designed in chewable dosage forms. For example, these compositions generally have sodium, calcium or magnesium carbonates present and in some cases aluminum hydroxide.

The processes of the present invention have also been shown to be especially useful in forming sweet and flavorful products which have less sugar present. For example, an artificial sweetener and/or flavor can be combined with corn syrup solids as the matrix and flash-flow processed with the inventive delivery system. The delivery system can then be diluted with non-sweet fillers such as starch or polydextrose and the like and added to the final product, e.g. a comestible, thereby reducing the amount of corn solids presenting the final product.

Invert sugar has also been found to be effective when used in the present delivery system, especially in combination with other flash-flavorable sweeteners because it produces a product having less hygroscopicity. Other materials which perform this function may also be used, as well as materials which hold water well, such as humectants, in applications where water content in the processing or final delivery system is to be controlled.

EXAMPLES

The following examples serve to provide further appreciation of the invention, but are not meant in any way to restrict the effective scope of the invention. Unless indicated otherwise, the Econo-Floss machine referred to above was used to form delivery systems.

EXAMPLE 1

Inventive delivery systems were prepared using sucrose as the matrix and spearmint flavor oil as the hydrophobic oil. In this example, 100 grams of sucrose were first hand mixed with 2 grams of spearmint flavor oil until a uniform mixture was obtained. The mixture was then flash-flow processed at a medium setting and approximately 3500 RPM. The resultant delivery system produced was a fine floss containing micronized droplets of flavor oil which was thereafter milled to a particle size of about 50 microns. The delivery system displayed rapid solubility and high flavor impact when placed in the mouth.

EXAMPLE 2

This example uses corn syrup solids as the matrix material, along with orange flavor oil and corn oil. In this example, 100 grams of corn syrup solids were hand mixed with 4 grams of orange flavor oil and 100 milligrams of sucralose. Thereafter, 2 grams of Mazola ® corn oil was geometrically added to the mixture using a mortar and pestle. The mixture was then flash-flow processed at a low setting to produce the inventive delivery systems having a flake-like appearance and sweet, orangy taste.

EXAMPLE 3

In this example, 100 grams of polydextrose K was hand mixed with 100 milligrams of the artificial high intensity sweetener sucralose until a uniform mixture was obtained. Thereafter, 2 grams of Mazola ® corn oil was geometrically added to the mixture using a mortar and pestle. The resultant mixture was then flash-flow processed at a low setting to produce the inventive delivery system having a chip-like appearance and intensive sweetness.

In Examples 4–6, the delivery systems prepared in Examples 1–3 are incorporated into chewing gum compositions in the amounts set forth below. The resultant chewing gum compositions display a rapid perception of flavor with up-front high impact.

EXAMPLE 4

| Chewing gum | |
|---|---|
| Ingredient | Percentage by Weight |
| Delivery System (Example 1) | 13.00 |
| Gum Base | 33.00 |
| Carbohydrates | 44.33 |
| Softeners | 9.50 |
| Colorant | 0.17 |
| | 100.00 |

EXAMPLE 5

| Sugarless Chewing Gum | |
|---|---|
| Ingredient | Percentage by Weight |
| Delivery System (Example 2) | 9.00 |
| Gum Base | 30.00 |
| Carbohydrates | 51.33 |
| Softeners | 9.50 |
| Colorant | 0.17 |
| | 100.00 |

EXAMPLE 6

| Sugarless Chewing Gum | |
|---|---|
| Ingredient | Percentage by Weight |
| Delivery System (Example 3) | 3.85 |
| Gum Base | 23.00 |
| Carbohydrates | 63.33 |
| Softeners | 9.50 |
| Colorant | 0.17 |
| Flavor Oil | 0.15 |
| | 100.00 |

In the following example, the delivery system of Example 1 was included in a pressed tablet to demonstrate that the soluble matrix also provides high flavor impact in comestibles other than chewing gums.

EXAMPLE 7

| Pressed Tablets | |
|---|---|
| Ingredient | Percentage by Weight |
| Delivery System (Example 1) | 22.00 |
| Sugar | 77.02 |
| Copper Gluconate (Breath Freshener) | 0.75 |
| Lubricant | 0.23 |
| | 100.00 |

Examples 8 and 9 demonstrate the use of the novel delivery systems in oral hygiene products. The high flavor impact provides an added organoleptic experience to otherwise mundane daily routines.

EXAMPLE 8

| Tooth Powder | |
|---|---|
| Ingredient | Percentage by Weight |
| Delivery System (Example 3) | 2.40 |
| Silica Hydrogel | 95.10 |
| Zinc Chloride | 0.50 |
| Sodium Fluoride | 0.22 |
| Sodium Gluconate | 0.28 |
| Sodium Methyl Cocoyltaurate | 1.50 |

-continued

| Tooth Powder | |
|---|---|
| Ingredient | Percentage by Weight |
| | 100.00 |

EXAMPLE 9

| Dentifrice Composition | |
|---|---|
| Ingredient | Percentage by Weight |
| Delivery System (Example 2) | 4.30 |
| Glycerin | 25.00 |
| Silicone Dioxide | 21.50 |
| HMP (Hexaphos) | 6.00 |
| Silica | 3.00 |
| Sodium Lauryl Sulfate | 1.20 |
| Sodium Hydroxide (50% solution) | 1.00 |
| Xanthan Gum | 1.00 |
| Sodium Benzoate | 0.50 |
| Titanium Dioxide | 0.50 |
| Fluoride | 0.22 |
| Deionized Water Q.S. | 100.00 |

EXAMPLE 10

This example is intended to demonstrate the use of amorphous micron-sized silica as adsorbent carriers for flavor oils which are incorporated into the inventive delivery systems for the purpose of achieving delayed release. A mixture of peppermint oil (75 gr.) and amorphous silica (75 gr.) (SYLOID 244 FP, Davison Chemical) was mixed in a Hobart mixer. This mixture is then added to polydextrose (2,348 gr.) and mixing is continued. The mixture is then flash-flow processed on an Econo-Floss spinning machine at 3600 RPM at 190° C. to yield a fine flake-like material. This delivery system is then incorporated in an amount of about 10% by weight into the chewing gum composition of Examples 4 and 5, in place of the delivery systems of Examples 1 and 2 respectively. The resultant chewing gum products demonstrated a delayed flavor release due to the affinity of the flavor for the silica and a reduced tendency of flavor oil to over-plasticize the gum base.

EXAMPLE 11

Examples 11 through 14 demonstrate the usefulness of the inventive delivery systems as dusting powders on chewing gum products, to aid in the rolling and scoring processes and prevent sticking and binding in the overall handling of the gum, both during processing and wrapping.

A flavor delivery system for delivery of up-front flavor in the form of a powder is prepared for use on the surface of a chewing product. 75 gr. of peppermint oil was mixed with 75 gr. of SYLOID 244FP (obtained from Davidson Chemical) to which 1.5 gr. of aspartame and 0.5 gr. of saccharin were added followed by mixing. This mixture was then gradually added to 2,348 gr. of Palatinit ® Type PF (an isomalt obtained from Sü Bungsmittel GmbH, Manheim, Germany) in a Hobart mixer. The mixture was then flash-flow processed on an Econo-Floss spinning machine at 3600 RPM at 190° C. yielding a white floss. The material was cryoground with liquid nitrogen to produce a fine white powder.

The powder was applied to the surface of a chewing gum mass which was then rolled between pressure rollers and formed into a slab. The powder adhering to the gum surface provided an immediate, pleasant sweet mint flavor when placed on the tongue.

EXAMPLE 12

The following flavor delivery system was prepared for use on the surface of a chewing gum product. 10.0 gr. of peppermint oil was mixed with 5.0 gr. of SYLOID 244FP to which 1.0 gr. of flour salt was added followed by mixing. This mixture was then gradually added to 394 gr. of Sucrose 10x in a Hobart mixer. The mixture was then flash-flow processed on an Econo-Floss spinning machine (which was modified to provide variable speed control and variable heat control) at 3,300 RPM at 190° C., yielding a white floss. The material was cryoground with liquid nitrogen to produce a fine white powder.

The powder was applied to the surface of a chewing gum mass which was then rolled between pressure rollers and formed into a slab. The powder adhering to the gum surface provided an immediate, pleasant sweet mint flavor when placed on the tongue.

EXAMPLE 13

The following flavor delivery system was prepared for use on the surface of a chewing gum product. 1.6 gr. of peppermint oil was mixed with 2 gr. of flour salt to which 2.0 gr. of aspartame was added followed by mixing. This mixture was then gradually added to 494.4 gr. of polydextrose in a Hobart mixer. The mixture was then flash-flow processed on an Econo-Floss spinning machine (which was modified to provide variable speed and variable heat) at 3300 RPM at 140° C. yielding a white floss. The material was cryoground with liquid nitrogen to produce a fine white powder.

The powder was applied to the surface of a chewing gum mass which was then rolled between pressure rollers and formed into a slab. The powder adhering to the gum surface provided an immediate, pleasant sweet mint flavor when placed on the tongue.

EXAMPLE 14

The following flavor delivery system was prepared for use on the surface of a chewing gum product. 100 gr. of peppermint oil was mixed with 5 gr. of SYLOID 244FP (obtained from Davison Chemical) to which 1.0 gr. of flour salt was added followed by mixing. This mixture was then gradually added to 394 gr. of corn syrup solid PE 36 (obtained from Hubinger) in a Hobart mixer. The mixture was then flash-flow processed on an Econo-Floss spinning machine (which was modified to provide variable heat and variable speed) at 3300 RPM at 145° C. yielding a white floss. The material was cryoground with liquid nitrogen to produce a fine white powder.

The powder was applied to the surface of a chewing gum mass which was then rolled between pressure rollers and formed into a chewing gum piece. The powder adhering to the gum surface provided an immediate, pleasant sweet mint flavor when placed on the tongue.

The powders of Examples 1–4 can also be used to provide up-front flavors bursts on mints, candies, baked goods, dentifrices, pharmaceuticals and the like.

EXAMPLES 15 and 16

The following flavor delivery systems were made in accordance with the process of the present invention using a spinning head temperature of about 140° C. for Example 15 and 190° C. for Example 16. Examples demonstrate the physical form of the delivery systems to be a matrix having a finely divided or micronized dispersion of flavor droplets distributed therein.

EXAMPLE 15

97% Maltrin—365 (a maltodextrin DE 36)
3% Peppermint Oil

EXAMPLE 16

97% Palatinit ® (an isomalt)
3% Peppermint Oil

Figure 2:
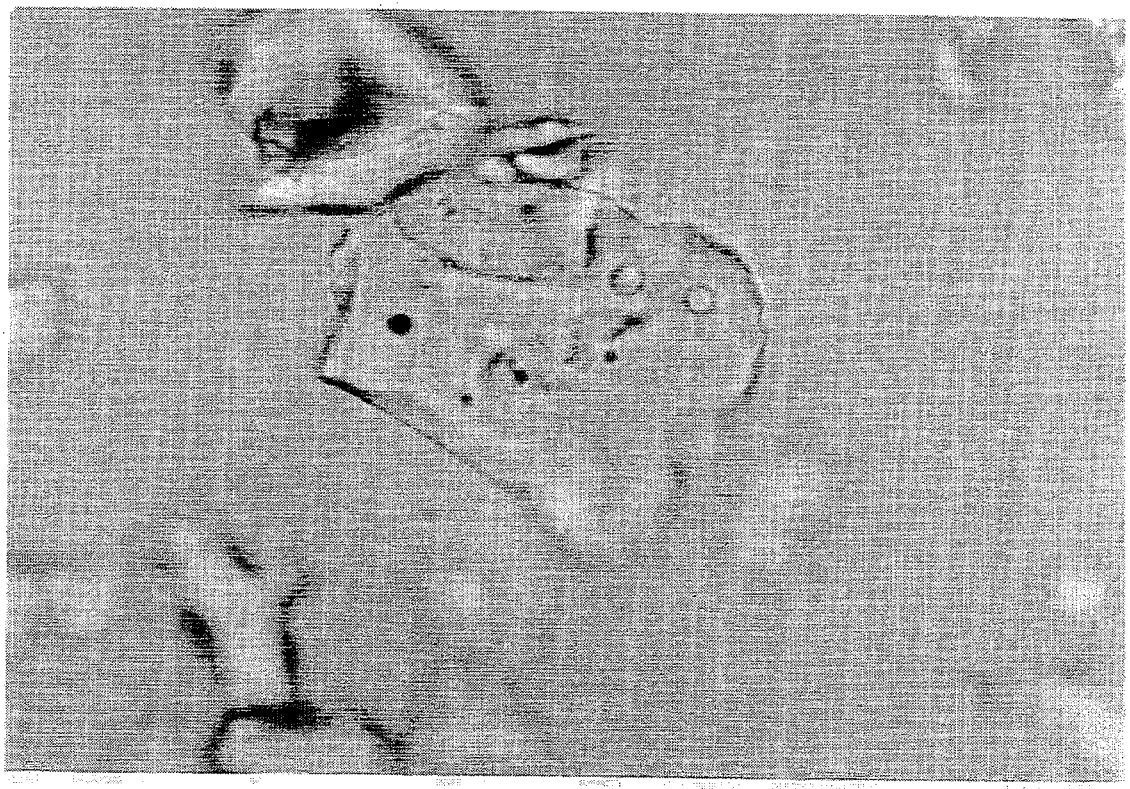
FIG. 2 is a photomicrograph (500×) showing micronized peppermint oil in a flash-flow-formed particulate matrix of Maltrin-365 which has undergone cryogrinding.

The delivery system of Example 15 was then photographed using conventional phase-contrast microscopy techniques to clearly discern the oil phase from the amorphous solid matrix. FIGS. 1 and 2 relate to Example 15, whereas FIGS. 3 and 4 relate to Example 16.

FIG. 1 is a photomicrograph at 500× magnification. The peppermint oil dispersion is clearly evident as those areas where birefringence (double circle areas) is present. The liquid can actually be seen to move within the encapsulated packet of the matrix and is easily discernable from air pockets, which lack both birefringence and movement.

FIG. 2 shows the delivery system of Example 15 at 1250× magnification subsequent to further comintion into a powder by cryogrinding with nitrogen. The minute flavor droplets are still present in the resultant powder, as seen in the birefringent areas of the photomicrograph, as well as through movement of the oil as seen under the microscope.

Figure 3:
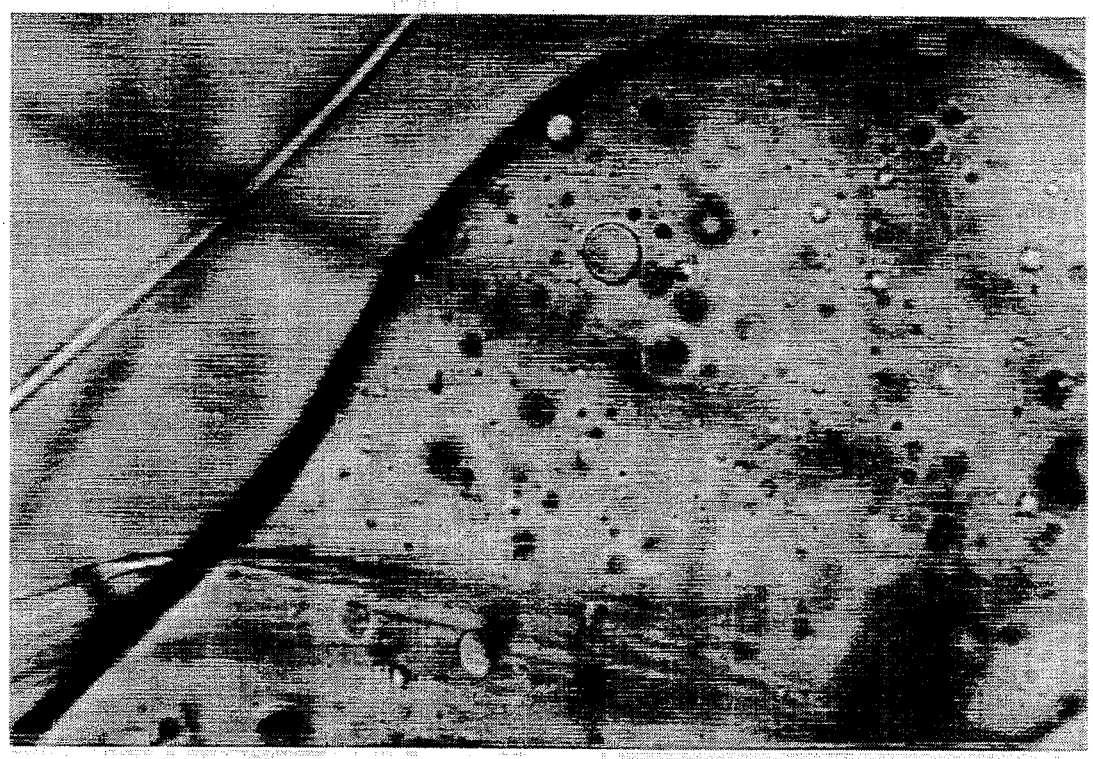
FIG. 3 is a photomicrograph (1250×) showing micronized peppermint oil in a flash-flow-formed matrix of an isomalt.

FIG. 3 is a photomicrograph (500×) of the delivery system of Example 16. Again the flavor dispersion is evident from the picture.

Figure 4:
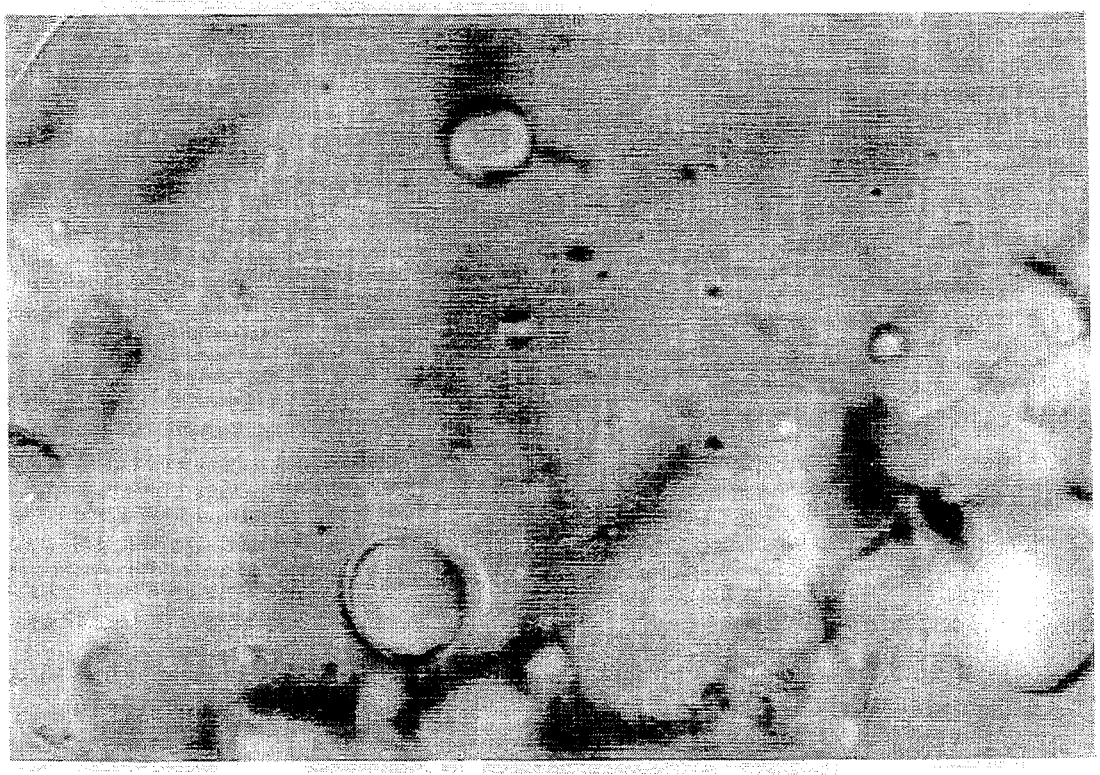
FIG. 4 is a photomicrograph (1250×) showing micronized peppermint oil in a flash-flow-formed particulate matrix of an isomalt which has undergone cryogrinding.

FIG. 4 shows the same delivery system subsequent to cryogrinding with nitrogen to a fine powder. The same physical results are present, demonstrating that the uniquely fine dispersion formed within the matrix remains even after grinding.

EXAMPLES 17-19

These examples are intended to demonstrate the ability of the inventive process and delivery system made therefrom to better protect the volatile flavor components.

A simple mixture of 92% Maltrin-365 (DE-36) and 8% peppermint oil was prepared in a Hobart mixer. This mixture was labelled Example 17. A sample of this mixture was used as the feedstock for preparing a delivery system of the present invention using an Econo-Floss machine (140° F., 3600 RPM). This delivery system was labelled Example 18.

Finally, a sample of Example 18 was croground using nitrogen and labelled Example 19.

Each of Examples 17, 18 and 19 were incubated in a temperature controlled environment (40° C.) for an extended period of time for the purpose of measuring volatile component loss, or in other words, determining relative flavor retention. FIG. 5 graphically depicts the percent oil remaining at various intervals of time. It is abundantly clear from the graph that the inventive delivery systems of the present invention (Examples 18 and 19) have retained the flavor over 168 hours at 40° C. significantly better than the simple mixture of Example 17. In fact, Example 18 shows only a nominal loss of flavors as compared to the simple mixture of Example 17. This is believed to be due to the unique physical properties resulting from the novel form of the delivery system.

While there have been described what are presently believed to be the preferred embodiments of the present invention, those skilled in the art will realize that changes and modifications may be made thereto without departing from the spirit of the invention, and it is intended to claim all such changes and modifications as fall within the true scope of the invention.

What is claimed is:

1. A solid delivery system for rapid release of hydrophobic liquids comprising a water-soluble flash-flow formed matrix containing a micronized dispersion of a substantially hydrophobic liquid.

2. The delivery system of claim 1 wherein the hydrophobic liquid is an oleaginous material.

3. The delivery system of claim 1 wherein the hydrophobic liquid is a flavor or fragrance oil.

4. The delivery system of claim 2 or 3 wherein the matrix is a sugar or sugar derivative.

5. The delivery system of claim 4 wherein the matrix is selected from the group consisting of sucrose, maltose, dextrose, ribose, fructose, lactose, glucose, arabinose, mannose, pentose, sorbose, xylose, galactose, sorbitol, mannitol, galactitol, lactitol, maltitol, maltooligosccharides, pentatol, isomalt, xylitol, sucralose, maltodextrin, polydextrose and derivatives and mixtures thereof.

6. The delivery system of claim 5 wherein the flavor oil is selected from the group consisting of natural and artificial flavors.

7. The delivery system of claim 6 wherein the flavor oil is a natural or synthetic plant oil or essence.

8. The delivery system of claim 7 wherein the flavor is selected from the group consisting of peppermint oil, spearmint oil, cinnamon oil, oil of wintergreen, nut oil, licorice, vanilla, citrus oils, fruit essences and mixtures thereof.

9. The delivery system of claim 8 wherein the citrus oil and fruit essences are selected from apple, apricot, banana, blueberry, cherry, coconut, grape, grapefruit, lemon, lime, orange, pear, peaches, pineapple, plum, raspberry, strawberry and mixtures thereof.

10. The delivery system of claim 4 wherein the oleaginous material is selected from the group consisting of a vegetable oil, mineral oil, or animal fat.

11. The delivery system of claim 10 wherein the oleaginous material is an edible oil.

12. The delivery system of claim 1 wherein the flash-flow-formed matrix is formed under conditions of flash heat, or flash shear.

13. The delivery system of claim 1 wherein the hydrophobic liquid is present in the matrix in a range of about 0.25% to about 40% by weight.

14. The delivery system of claim 5 wherein there is additionally incorporated a sweetener selected from the group consisting of dipeptide and amino acid-based sweeteners, saccharin salts and its free acid, cyclamate salts, acesulfame and its salts, hydrogenated starch hydrolysate, talin, thaumatin, steroside, dihydrochalcone and mixtures thereof.

15. A method of producing particulates useful for delivering hydrophobic liquids, said particulates having dispersed therein a micronized hydrophobic liquid, comprising the step of subjecting a flash-flowable material to flash-flow conditions to form a solid particulate comprising a matrix of the flash-flowable material containing a micronized dispersion of the hydrophobic liquid.

16. The method of claim 15 wherein the solid matrix is reduced to finer particles by grinding, pulverizing or sieving.

17. The method of claim 16 wherein the solid matrix is reduced to finer particles by cryogrinding.

18. The method of claim 15 wherein the flash-flowable material is a saccharide-based compound.

19. The method of claim 18 wherein the flash-flowable material is selected from the group consisting of sucrose, maltose, dextrose, ribose, fructose, lactose, glucose, arabinose, mannose, pentose, xylose, galactose, sorbitol, mannitol, galactitol, lactitol, maltitol, maltooligosaccharides, pentatol, isomalt, xylitol, sucralose, maltodextrin, polydextrose and derivatives and mixtures thereof.

20. The method of claim 15 wherein the flash-flowable matrix additional incorporates a flash-flowable non-saccharide based polymer.

21. The method of claim 20 wherein the non-saccharide based polymer is a thermoplastic or cellulosic.

22. The method of claim 15 wherein the hydrophobic liquid is a flavor or fragrance oil.

23. The method of claim 15 wherein the flash-flowable material and/or the hydrophobic oil is pre-mixed with a material selected from the group consisting of fillers, sweeteners, coloring agents, humectants, plasticizers, emulsifiers and mixtures thereof.

24. The method of claim 23 wherein the pre-mix comprises a flavor oil and a sweetener.

25. The method of claim 15 wherein the flavor oil is absorbed onto a carrier material prior to flash-flow processing.

26. The method of claim 15 wherein the flash-flowable material is a synthetic amorphous silica or porous maltodextrin aggregate.

27. The chewing gum composition comprising:
a) a gum base; and
b) a solid sweetener and flavor delivery system comprising a water-soluble flash-flow-form matrix containing a micronized dispersion of flavor oil.

28. The chewing gum composition of claim 27 wherein the water-soluble flash-flow-formed matrix is a saccharide-based material.

29. The chewing gum composition of claim 27 wherein the flavor oil is pre-mixed with a synthetic amorphous silica prior to incorporation in the matrix.

30. A chewing gum product having a core portion comprising gum base, sweetener and flavor and having deposited on the surface of said core portion a powdered rolling material comprising particles of flash-flow-formed saccharide-based material containing a micronized dispersion of a flavor oil.

31. The chewing gum product of claim 30 wherein the saccharide-based material is selected from the group consisting of sucrose, maltose, dextrose, ribose, fructose, lactose, glucose, arabinose, mannose, pentose, xylose, galactose, sorbitol, mannitol, galactitol, lactitol, maltitol, maltooligosaccharides, pentatol, isomalt, xylitol, sucralose, maltodextrin, polydextrose and derivatives and mixtures thereof.

32. The chewing gum product of claim 31 wherein the saccharide-based material contains an artificial sweetener.

33. A comestible product having enhanced flavor and sweetness comprising an edible flash-flow-formed delivery system having micronized dispersion of a flavor oil and/or a sweetener contained in a water-soluble flash-flowable material.

34. The comestible product of claim 33 wherein the flash-flowable material is a saccharide-based material.

35. A flash-flow-formed sweetener delivery system comprising a solid amorphous saccharide-based matrix material and an artificial sweetener dispersed therein.

36. A delivery system for flavors and sweeteners comprising a flash-flowable saccharide-based matrix containing a sweetener or flavor dispersed therein formed by flash-flow processing.

37. The delivery system of claim 1 incorporated into a cosmetic composition.

38. The delivery system of claim 1 incorporated into a dentifrice composition.

39. The delivery system of claim 4 incorporated into a comestible.

40. The delivery system of claim 4 incorporated into a confectionery product.

41. The delivery system of claim 4 incorporated into a baked product.

* * * * *